United States Patent
Sanpietro (10) Patent No.: US 6,692,470 B2
(45) Date of Patent: *Feb. 17, 2004

(54) SINGLE-USE HYPODERMIC SYRINGE HAVING A REMOVABLE NEEDLE ASSEMBLY

(75) Inventor: Joseph A. Sanpietro, Freehold, NJ (US)

(73) Assignee: Medi-Hut Co., Inc., Lakewood, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/488,807

(22) Filed: Jan. 21, 2000

(65) Prior Publication Data
US 2003/0028149 A1 Feb. 6, 2003

(51) Int. Cl.[7] .................................. A61M 5/32
(52) U.S. Cl. ........................ 604/198; 604/197
(58) Field of Search ................. 604/192, 197, 604/198, 163, 164.08, 110

(56) References Cited

U.S. PATENT DOCUMENTS

| 5,562,624 | A | * | 10/1996 | Righi et al. | ............. | 604/110 |
| 5,562,626 | A | * | 10/1996 | Sanpietro | .............. | 604/110 |
| 5,658,254 | A | * | 8/1997 | Reichenbach et al. | ....... | 604/110 |
| 5,817,064 | A | * | 10/1998 | DeMarco et al. | ........... | 604/198 |
| 5,843,041 | A | * | 12/1998 | Hake et al. | ............... | 604/198 |

FOREIGN PATENT DOCUMENTS

| WO | WO 99/37345 | * | 7/1999 | ........... | A61M/5/32 |

* cited by examiner

Primary Examiner—Brian L. Casler
Assistant Examiner—Catherine Serke
(74) Attorney, Agent, or Firm—Duane Morris LLP (57) ABSTRACT

A single-use hypodermic syringe having a syringe barrel with distal and proximal ends. The syringe barrel includes a flange at the proximal end thereof and a luer locking collar at the distal end thereof. A needle assembly is removably coupled to the distal end of the syringe barrel. The needle assembly includes a hub and a needle extending from a distal end of the hub. A plunger is telescopically positionable within the barrel. A tubular shield is disposed around the syringe barrel such that the syringe barrel can be moved relative thereto. The shield includes locking prongs extending proximally therefrom, and a spring for moving the syringe barrel from an unused position, where the shield allows exposure of the needle assembly, into a used position where the shield covers the needle assembly. The prongs engage the syringe barrel flange to retain the barrel in the unused position, and disengage from the barrel flange during use of the syringe thereby permitting the spring to move the barrel into the used position. The needle assembly is provided with an expandable collar (expansion collar) that coacts with the shield to maintain the barrel in the used position. The hub and the expansion collar are formed as a single unitary part. The expansion collar is preferably provided with four locking tabs. The prongs of the shield include circular hook segments for engaging the syringe barrel flange to retain the barrel in the unused position.

18 Claims, 7 Drawing Sheets

SINGLE-USE HYPODERMIC SYRINGE HAVING A REMOVABLE NEEDLE ASSEMBLY

FIELD OF THE INVENTION

This invention relates to single-use hypodermic syringes, and in particular to a single-use hypodermic syringe having a needle assembly which can be changed prior to use of the syringe.

BACKGROUND OF THE INVENTION

Contagious diseases can be transferred by reusing hypodermic syringes that are intended for single use. The reuse and sharing of such syringes is especially common among intravenous drug users. This places intravenous drug users at high risk for contracting the AIDS virus and encourages the proliferation of drug abuse. Further, the frequent re-use of hypodermic syringes in mass inoculation programs is a problem in certain countries. Such reuse may be responsible for the spread of many diseases in these countries. Additionally, healthcare personnel and other people who handle used syringes are often accidentally stuck with syringes during disposal or destruction thereof.

The problem of hypodermic syringe re-use has been addressed in many ways through the years. One early solution involved destroying the syringe after use. Other solutions involved providing certain methods and devices which the user would employ to destroy or render the syringe inoperable. Unfortunately, these methods and devices are not effective with users who intend to re-use syringes or when the syringe is accidentally mishandled.

A more recent solution has been to provide protective shields that automatically cover the needle of the syringe after use. An example of such a syringe is disclosed in U.S. Pat. No. 5,562,626. The syringe disclose therein is provided with a shield or sheath that automatically extends over and covers the needle of the syringe after the syringe has been used Although the syringe of U.S. Pat. No. 5,562,626 operates very satisfactorily, it does have a couple of drawbacks. One drawback is that the needle assembly typically employs a small bore needle (25 to 20 gage) which provides for a relatively painless injection. The needle assembly is permanently affixed to the tapered neck of the syringe barrel by an adhesive. This makes it impossible to mount a different needle assembly to the syringe in situations where for example, a large bore needle (18–16 gage) would be desirable to facilitate quick filling of the syringe. Moreover, the needle assembly includes a separately manufactured expansion collar (which forms part of the mechanism which prevents movement of the shield to uncover the needle after use) which undesirably increases the cost of the syringe.

Another drawback of the syringe disclosed in U.S. Pat. No. 5,562,626 is that it incorporates a safety bushing which must to be removed in order to operate the plunger assembly of the syringe. This safety bushing further adds to the cost of the syringe and makes the syringe more complicated to use.

Accordingly, a need exists for a single-use hypodermic syringe which permits changing of the needle assembly, is inexpensive to manufacture, and convenient to operate.

SUMMARY OF THE INVENTION

A single-use hypodermic syringe comprises a syringe barrel with distal and proximal ends. The syringe barrel includes a flange at the proximal end thereof and a luer locking collar at the distal end thereof. A needle assembly is removably coupled to the distal end of the syringe barrel. The needle assembly includes a hub and a needle extending from a distal end of the hub. A plunger is telescopically positionable within the barrel. A tubular shield is disposed around the syringe barrel such that the syringe barrel can be moved relative thereto. The shield includes locking prongs extending proximally therefrom, and a spring for moving the syringe barrel from an unused position, where the shield allows exposure of the needle assembly, into a used position where the shield covers the needle assembly. The prongs engage the syringe barrel flange to retain the barrel in the unused position, and disengage from the barrel flange during use of the syringe thereby permitting the spring to move the barrel into the used position.

One aspect of the invention involves providing the needle assembly with an expandable collar (expansion collar) that coacts with the shield to maintain the barrel in the used position. More specifically, the expansion collar expands to engage a locking protrusion provided on the shield protrusion when the barrel is moved to the used position.

Another aspect of the invention involves forming the hub and expansion collar as a single unitary part.

Still another aspect of the invention involves providing the expansion collar with four locking tabs.

A further aspect of the invention involves providing circular hook segments on the prongs for engaging the syringe barrel flange to retain the barrel in the unused position.

BRIEF DESCRIPTION OF THE DRAWINGS

The advantages, nature, and various additional features of the invention will appear more fully upon consideration of the illustrative embodiment now to be described in detail in connection with accompanying drawings wherein.

It should be understood that the drawings are for purposes of illustrating the concepts of the invention and are not to scale.

DETAILED DESCRIPTION OF THE INVENTION

Figure 1:
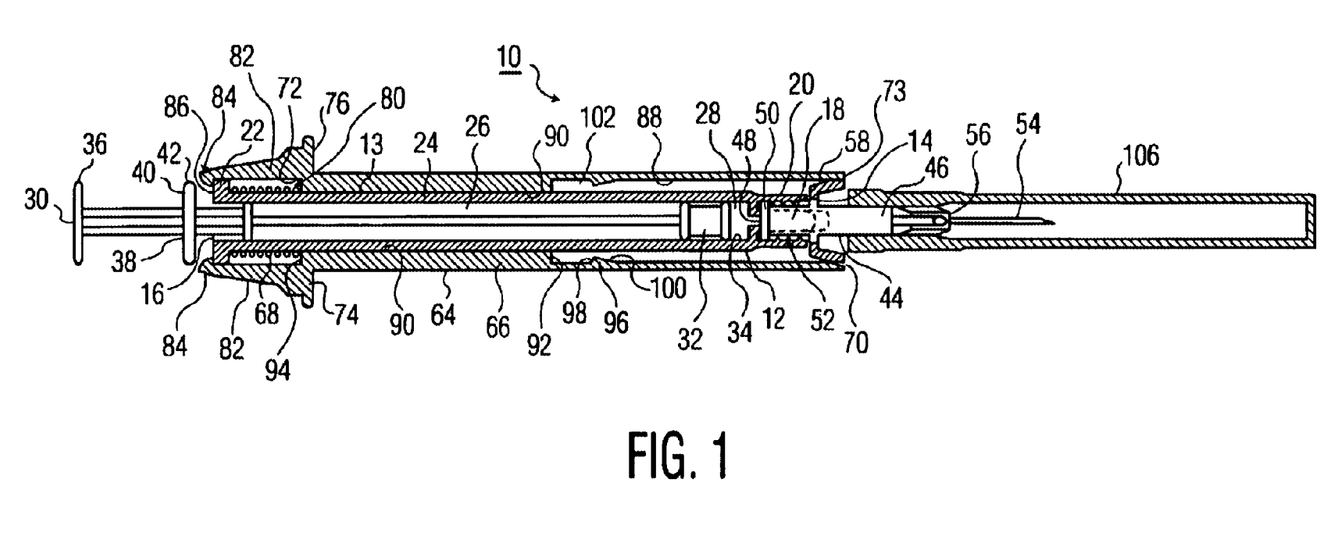
FIG. 1 is a partial cross-sectional view of a single-use syringe according to an embodiment of the invention, shown in an unused condition.
Figure 2:
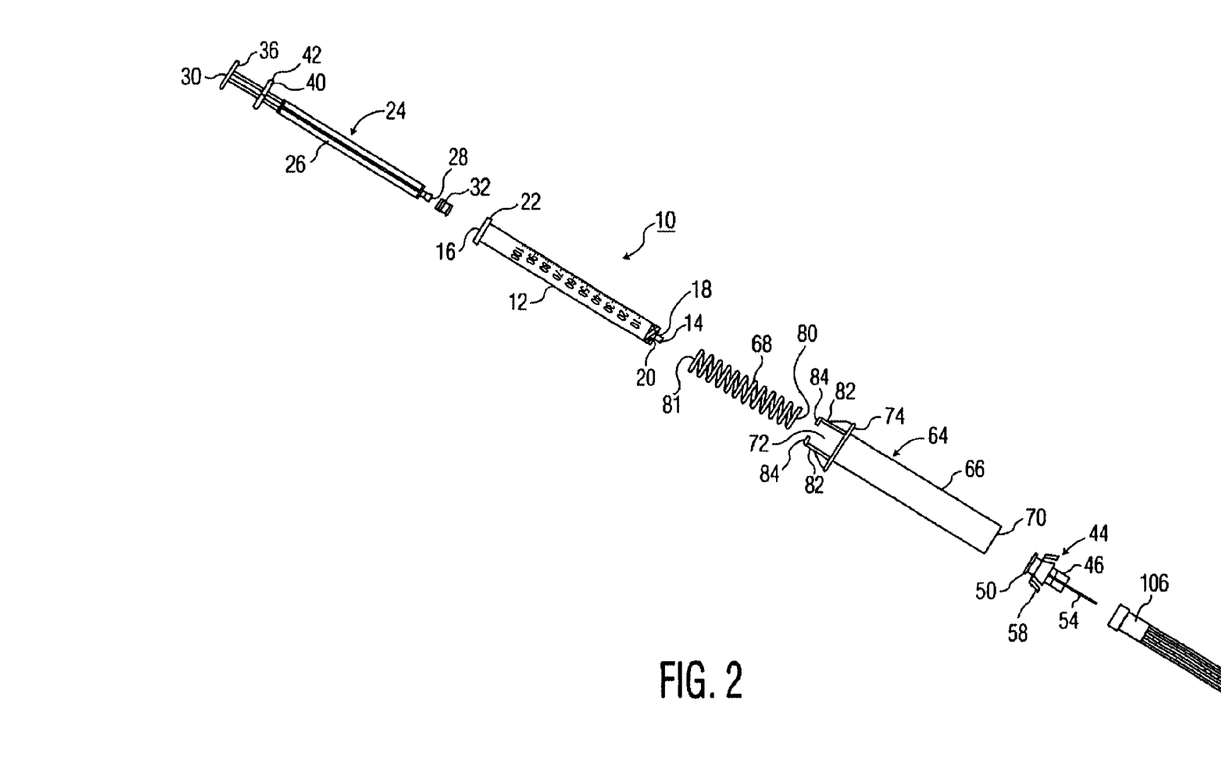
FIG. 2 is an exploded view of the syringe of FIG. 1.
Figure 7A:
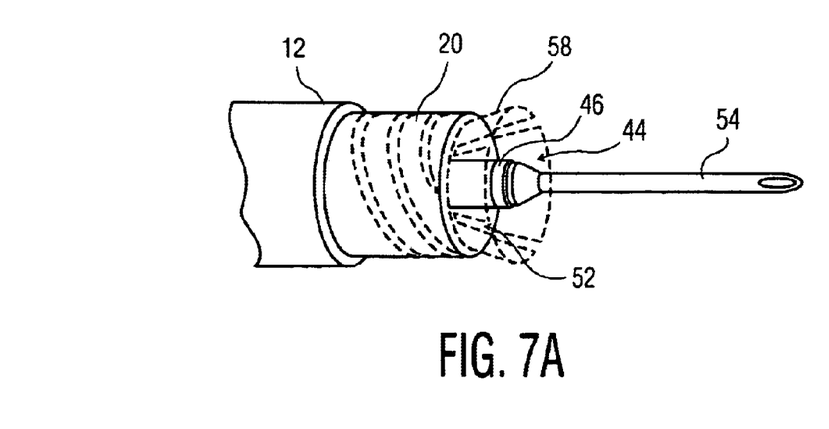
FIG. 7A is an enlarged elevational view of a luer lock arrangement employed in the syringe of the invention.
Figure 7B:
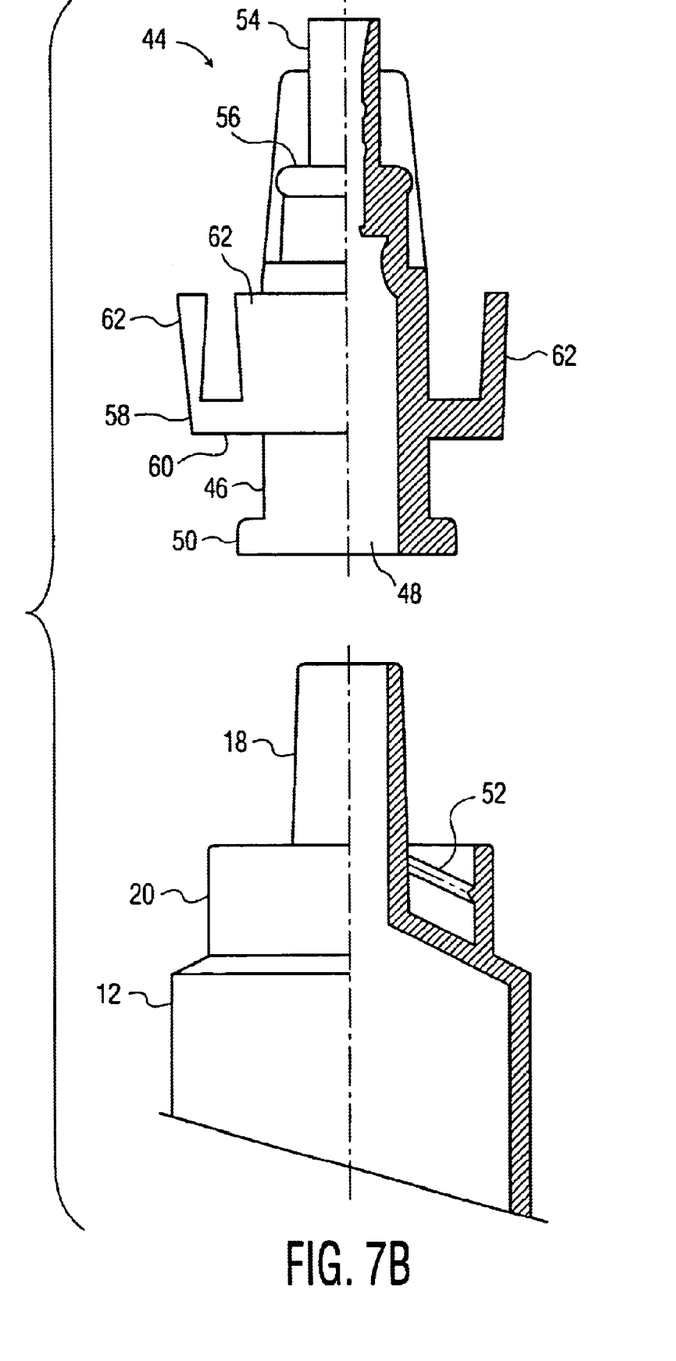
FIG. 7B is an exploded partial sectional view of the distal end of a syringe barrel employed in the invention and the needle assembly.

FIGS. 1 and 2 collectively show a single use syringe 10 according to an embodiment of the invention. The syringe 10 includes a hypodermic syringe barrel 12 with a partially closed distal end 14 (the end farthest from the user), and an open proximal end 16 (the end closest to the user). The syringe barrel 12 can be any size depending upon the intended use of the syringe 10 and the volume of solution to be handled. The distal end 14 of the syringe barrel 12 conventionally includes an elongated generally cylindrical tip 18 that permits the passage of fluid from the barrel 12, and an internally threaded luer locking collar 20 that surrounds the tip 18 (FIG. 7B). The proximal end 16 of the syringe barrel 12 includes an outwardly extending annular flange 22.

A plunger assembly 24 is reciprocally disposed in the syringe barrel 12. The plunger assembly 24 includes a plunger shaft 26 with distal and proximal ends 28, 30. A conventional elastomeric stopper 32 is attached to the distal end 20 of the plunger shaft 26 in a typical manner. The stopper 32 sealingly engages the inner surface 34 of the syringe barrel 12 so that when the plunger assembly 24 is reciprocated in the syringe barrel 12, liquid is displaced from, or drawn into the barrel 12. The proximal end 30 of the plunger shaft 26 extends through the open proximal end 16 of the syringe barrel 12 and includes in a conventional finger push flange 36. A circular trigger flange 40 surrounds the marginal proximal end 30 of the plunger shaft 26. The trigger flange 40 has a rounded peripheral edge surface 42.

Figure 5A:
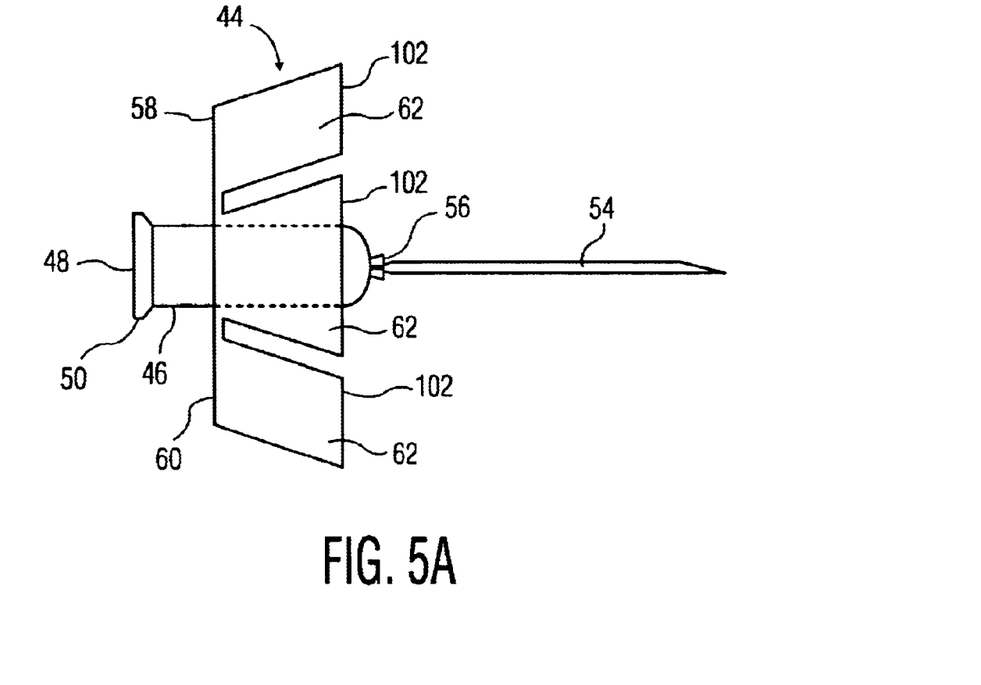
FIG. 5A is an elevational view of a needle assembly employed in the syringe of invention.
Figure 5B:
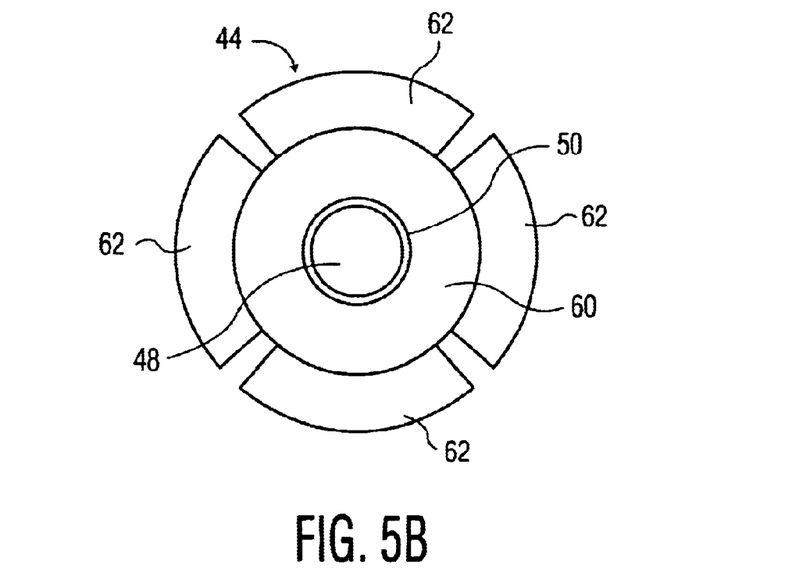
FIG. 5B is a proximal end view of the needle assembly of FIG. 5A.

A needle assembly 44 is removably installed over the tip 18 of the syringe barrel 12 via the luer locking collar 20. The needle assembly 44 includes a generally cylindrical hub 46 with an open proximal end 48 that leads to the interior of the hub 46 for receiving the tip 18 of the syringe barrel 12. An outwardly projecting circumferential lip 50 surrounds the proximal open end 48 of the hub 46. A hollow needle 54 is affixed to a distal end 56 of the hub 46 and communicates with the hub's interior. The needle 54 is typically a small bore design (25 to 20 gage) that provides for a relatively painless injection. An expandable collar 58 (expansion collar 58) is disposed about the hub 46 of the needle assembly 44 between the distal and proximal ends 56, 48 thereof. As shown in FIGS. 5A and 5B, the expansion collar 58 has an annular base 60 and preferably four (4) outwardly inclined locking tabs 62 which are hinged to a peripheral area of the base 60 and extend distally therefrom. The expansion collar 58 and the hub 46 are formed as a single unitary plastic part using conventional plastic molding methods.

The needle assembly 44 employed in the invention advantageously reduces the cost of the syringe 10 due to the unitary construction of the hub 46 and expansion collar 58. Further, the luer locking arrangement formed by the hub lip 50 and the threaded inner surface 52 of the barrel collar 20 (FIG. 7B), enable the needle assembly 44 to be easily replaced with a conventional needle assembly (not shown) employing a large bore needle (to facilitate quick filling of the syringe, etc.) prior to use of the syringe 10. Additionally, the collar's 58 preferred arrangement of only four outwardly inclined locking tabs 62 makes it more difficult to return the syringe 10 to a "ready-to-use" position.

Figure 6A:
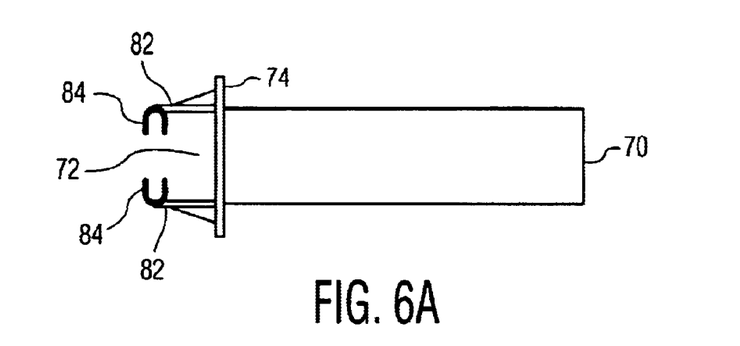
FIG. 6A is an elevational view of a safety needle shield employed in the syringe of the invention.

Referring again to FIGS. 1 and 2 along with FIG. 6A, the syringe 10 further includes a moveable needle safety shield assembly 64 which operates to cover the needle 54 after the syringe 10 is used as will be explained further on. The safety shield assembly 64 has a tubular needle safety shield 66 and a coil-type spring 68 disposed between the annular flange 22 of the syringe barrel 12 and the needle shield 66. The needle shield 66 has distal and proximal open ends 70, 72. The distal open end 70 includes a beveled inner lead-in surface 73 which facilitates entry of the expansion collar 58. A finger flange 74 surrounds the proximal open end 72 of the needle shield 66 to provide a surface 76 upon which two fingers of a user's hand may rest when using the safety syringe 10. Two oppositely disposed elastically flexible prongs 82 extend proximally from the finger flange 74 of the needle shield 66. The proximal end 83 of each prong 82 includes a semi-annular hook 84. The hooks 84 are oriented on the prongs 82 so that they face each other, and the proximal-most surface 86 of each hook 84 is inwardly beveled.

Figure 6B:
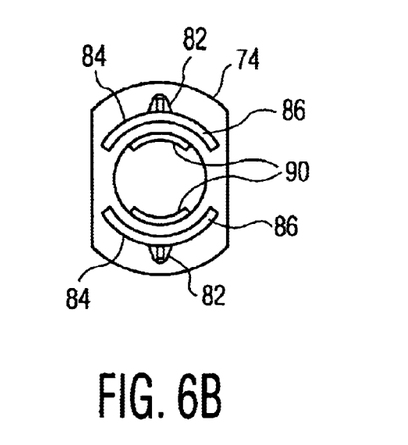
FIG. 6B is a proximal end view of the safety needle shield of FIG. 6A.

As shown in FIG. 6B, the semi-annular hooks 84 wrap around and securely grip the annular flange 22 of the syringe barrel 12 to position the needle shield 66 proximally on the syringe in the earlier mentioned "ready-to-use" position. In this position, the needle shield 66 substantially compresses the spring 68 and exposes the needle 54 of the needle hub assembly 44. The semi-annular design of the hooks 84 grip a large area of the annular flange 22, advantageously eliminating additional safety guards used in conventional syringes.

Figure 3:
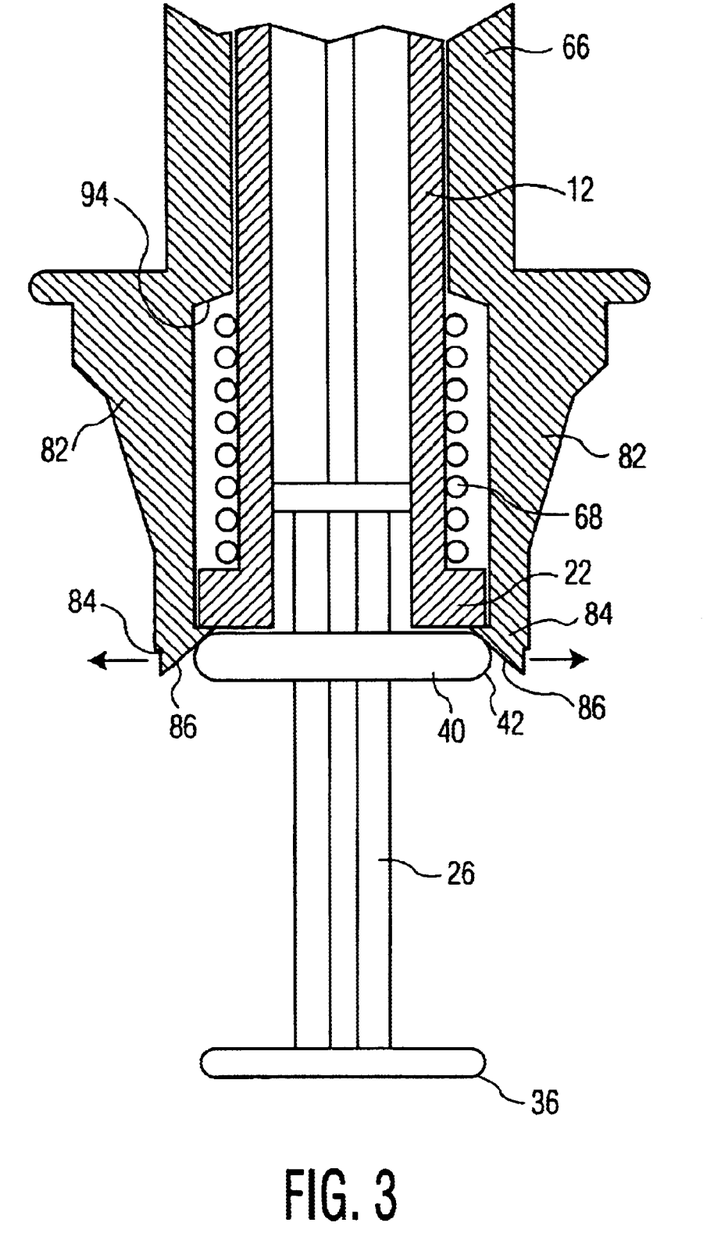
FIG. 3 is an enlarged cross-sectional view showing the how the plunger assembly and the safety shield assembly cooperate when the syringe of FIG. 1 is used.

As shown in FIGS. 1, 3 and 6B, the inner surface 88 of the tubular needle shield 66 is generally cylindrical with two oppositely disposed inwardly projecting arcuate segments 90 which slidingly engage the outer surface 13 of the syringe barrel 12. The arcuate segments 90 extend distally, partially down the length of the needle shield 66 from the proximal end 16 thereof. The arcuate segments 90 have distal and proximal end surfaces 92, 94. The distal end 80 of the spring 68 abuts against the proximal end surfaces 94 of the arcuate segments 90 and the proximal end 81 of the spring 68 abuts against the annular flange 22 of the syringe barrel 12. Spaced distally from the arcuate segments 90 on the inner surface 88 of the needle shield 66 is an annular locking projection 96. The locking projection 96 has a locking surface 98 which faces the distal end surfaces 92 of the arcuate segments 90, and an inclined surface 100 which provides a smooth transition from the inner surface 88 of the shield 66 to locking surface 98 thereof.

A needle cap 106 is provided for protecting the unused needle 54. The needle cap 106 slidingly engages the hub 46 of the needle assembly 44 in an interference fit. The needle cap 106 is removed prior to using the syringe. 10.

The syringe 10 is filled and operated in a conventional manner. If desired, the needle assembly 44 can be removed via the luer locking arrangement formed by the hub lip 50 and the threaded inner surface 52 of the barrel collar 20, and replaced with a conventional needle assembly employing a large bore needle to facilitate quick filling of the syringe. During injection, the plunger assembly 24 is advanced distally into the syringe barrel 12 by squeezing the finger and push flange 74 together. As the plunger assembly 24 advances into the syringe barrel 12, the rounded peripheral edge surface 42 of the plunger shaft trigger flange 40 engages the beveled proximal surfaces 86 of the semi-annular hooks 84, thereby spreading apart the prongs 82 and disengaging the hooks 84 from the annular flange 22 of the syringe barrel 12 as shown in FIG. 3. Just as the hooks 84 disengage, the trigger flange 40 abuts against the annular flange 22.

Figure 4:
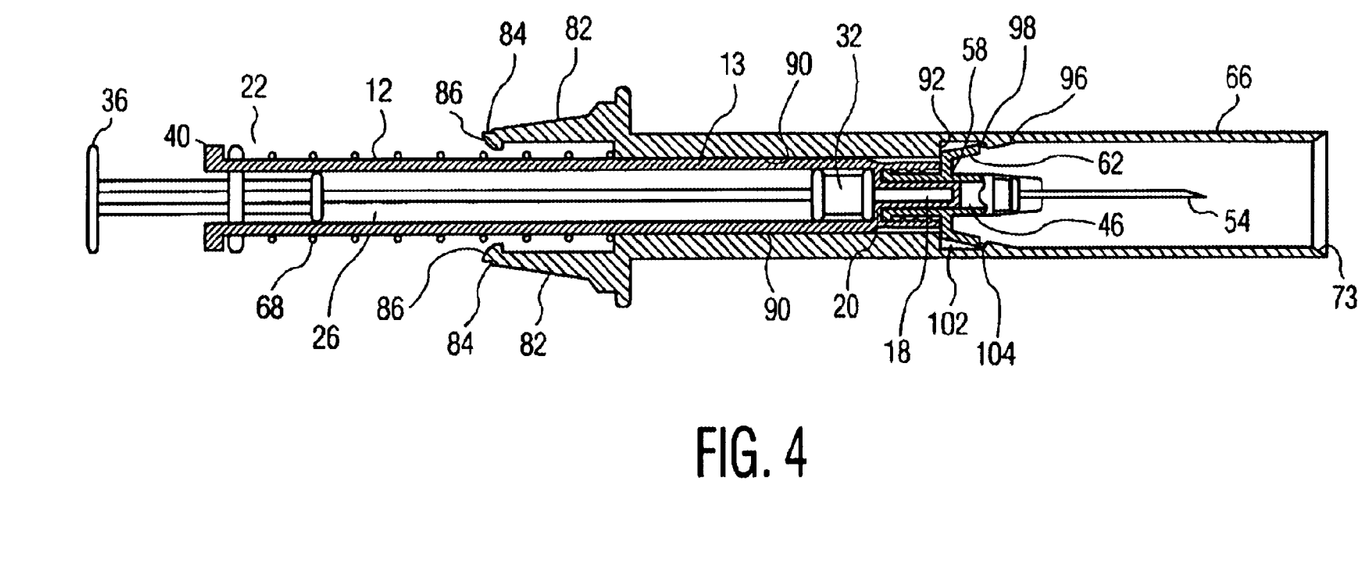
FIG. 4 is a partial cross-sectional view of the syringe of FIG. 1, shown in a used condition.

Immediately after completion of injection, the natural act of releasing the squeezing pressure permits the spring 68 which is compressed between the annular flange 12 and the arcuate segments 90, to urge the plunger assembly 24 and syringe barrel 12 proximally past the hooks 84. Because the trigger flange 40 and the annular flange 22 are abutted against one another, the hooks 84 are unable to recapture the annular flange 22. As the syringe barrel 12 moves proximally relative to the needle shield 66, the needle assembly 44 enters the distal end of the needle shield 66. The locking tabs 62 of the expansion collar 58 pivot radially inward as they slide over the inclined surface 100 of the locking projection 96. Just as the locking tabs 62 move past the projection 96, they pivot radially outward due to the resilient nature of the expansion collar 58, and engage the inner surface 88 of the needle shield 66 in the space 102 between the arcuate segments 90 and the locking projection 96 as shown in FIG. 4. Any attempt at moving the syringe barrel 12 distally relative to the needle shield 66 to expose the needle 54 again is prevented by the distal ends 104 of the expansion collar locking tabs 62 abutting against the locking surface 98 of the locking projection 96.

While the foregoing invention has been described with reference to the above embodiment, various modifications and changes can be made without departing from the spirit of the invention. Accordingly, all such modifications and changes are considered to be within the scope of the appended claims.

What is claimed is:

1. A single-use hypodermic syringe comprising:
   a syringe barrel having distal and proximal ends, the syringe barrel having a flange at the proximal end thereof;
   a needle assembly removably coupled to the distal end of the syringe barrel, the needle assembly including a hub, a needle extending from a distal end of the hub, and an expandable collar, the hub extending through the collar;
   a plunger telescopically positionable within the barrel;
   a tubular shield disposed around the syringe barrel such that the syringe barrel can be moved relative thereto, the shield including at least one locking prong extending proximally therefrom, the at least one locking prong including a semi-annular hook; and
   a spring for moving the syringe barrel from an unused position, where the shield allows exposure of the needle assembly, into a used position where the shield covers the needle assembly, the semi-annular hook engaging the syringe barrel flange to retain the barrel in the unused position, the semi-annular hook disengaging from the barrel flange during use of the syringe thereby permitting the spring to move the barrel into the used position, the expandable collar coacting with the shield to maintain the barrel in the used position.

2. The syringe according to claim 1, wherein the shield includes a locking protrusion, the collar expanding to engage the protrusion when the barrel is moved to the used position.

3. The syringe according to claim 1, wherein the hub and collar are a single unitary part.

4. The syringe according to claim 1, wherein the collar includes four locking tabs.

5. The syringe according to claim 1, wherein the plunger includes a trigger flange which disengages the semi-annular hook from the syringe barrel flange during use of the syringe thereby permitting the spring to move the barrel into the used position.

6. The syringe according to claim 1, wherein the expandable collar includes at least one locking tab extending outwardly from the hub, the at least one tab coacting with the shield to maintain the barrel in the used position.

7. The syringe according to claim 1, wherein the expandable collar includes a base and at least one inclined locking tab hinged to the base, the at least one tab coacting with the shield to maintain the barrel in the used position.

8. A single-use hypodermic safety syringe comprising:
   a syringe barrel having distal and proximal ends, the syringe barrel having a flange at the proximal end thereof;
   a needle assembly coupled to the distal end of the syringe barrel;
   a plunger telescopically positionable within the barrel;
   a tubular shield disposed around the syringe barrel such that the syringe barrel can be moved relative thereto, the shield including locking prongs extending proximally therefrom, the prongs each terminating with a semi-annular hook; and
   a spring for moving the syringe barrel from an unused position, where the shield allows exposure of the needle assembly, into a used position where the shield covers the needle assembly, the semi-annular hooks engaging the barrel flange to retain the barrel in the unused position, the semi-annular hooks disengaging from the barrel flange during use of the syringe thereby permitting the spring to move the barrel into the used position.

9. The syringe according to claim 8, wherein the needle assembly includes a hub and a needle extending from a distal end of the hub.

10. The syringe according to claim 9, wherein the needle assembly further includes an expandable collar, the hub extending through the collar.

11. The syringe according to claim 10, wherein the shield includes a locking protrusion, the collar expanding to engage the protrusion when the barrel is moved to the used position.

12. The syringe according to claim 10, wherein the distal end of the syringe barrel includes a luer locking collar removably coupling the hub to the distal end of the barrel.

13. The syringe according to claim 9, wherein the distal end of the syringe barrel includes a luer locking collar removably coupling the hub to the distal end of the syringe barrel.

14. The syringe according to claim 8, wherein the plunger includes a trigger flange that disengages the semi-annular hooks from the syringe barrel flange during use of the syringe thereby permitting the spring to move the barrel into the used position.

15. A single-use hypodermic syringe comprising:
   a syringe barrel having distal and proximal ends, the syringe barrel having a flange at the proximal end thereof;
   a needle assembly coupled to the distal end of the syringe barrel, the needle assembly including a hub, a needle extending from a distal end of the hub, and at least one inclined locking tab extending outwardly from the hub;
   a plunger telescopically positionable within the barrel;
   a tubular shield disposed around the syringe barrel such that the syringe barrel can be moved relative thereto, the shield including locking prongs extending proximally therefrom, the prongs each terminating with a semi-annular hook; and
   a spring for moving the syringe barrel from an unused position, where the shield allows exposure of the needle assembly, into a used position where the shield covers the needle assembly, the semi-annular hooks engaging the syringe barrel flange to retain the barrel in the unused position, the semi-annular hooks disengaging from the flange during use of the syringe thereby permitting the spring to move the barrel into the used position.

16. The syringe according to claim 15, wherein the shield includes a locking protrusion, the at least one locking tab engaging the protrusion when the barrel is moved to the used position.

17. The syringe according to claim 15, wherein the distal end of the syringe barrel includes a luer locking collar removably coupling the hub to the distal end of the syringe barrel.

18. The syringe according to claim 15, wherein the plunger includes a trigger flange that disengages the semi-annular hooks from the syringe barrel flange during use of the syringe thereby permitting the spring to move the barrel into the used position.

* * * * *